United States Patent [19]

Satomi et al.

[11] 3,936,433

[45] Feb. 3, 1976

[54] O-ETHYL-O-)3-METHYL-6-NITROPHENYL)-N-SECONDARY BUTYL-PHOSPHOROTHIONOAMIDATE

[75] Inventors: Takeo Satomi, Takarazuka; Kunio Mukai, Nishinomiya; Akihiko Mine; Naganori Hino, both of Toyonaka; Kohshi Tateishi; Masachika Hirano, both of Minoo, all of Japan

[73] Assignee: Sumitomo Chemical Company, Limited, Osaka, Japan

[22] Filed: May 29, 1974

[21] Appl. No.: 474,444

Related U.S. Application Data

[63] Continuation-in-part of Ser. No. 182,523, Sept. 21, 1971, abandoned.

[30] Foreign Application Priority Data

Sept. 25, 1970 Japan.............................. 45-84432

June 1, 1973 United Kingdom............... 26377/73

[52] U.S. Cl..................................... 260/954; 71/87
[51] Int. Cl.$^2$........................ C07F 9/24; A01N 9/36
[58] Field of Search..................................... 260/954

[56] References Cited

UNITED STATES PATENTS 3,787,538   1/1974   Schrader et al..................... 260/954

*Primary Examiner*—Anton H. Sutto
*Attorney, Agent, or Firm*—Wenderoth, Lind & Ponack

[57] ABSTRACT

O-alkyl-O-)3-methyl-6-nitrophenyl)-N-secondary butyl-phosphorothionoamidate, which possesses herbicidal properties.

1 Claim, No Drawings

O-ETHYL-O-(3-METHYL-6-NITROPHENYL)-N-SECONDARY BUTYL-PHOSPHOROTHIONOAMIDATE

This application is a continuation-in-part of the copending application Ser. No. 182,523 filed Sept. 21, 1971, now abandoned.

The present invention relates to the new phosphothionoamidate, to the herbicidal composition and to the use as a herbicide.

More particularly, the present invention pertains to the compound of the formula,

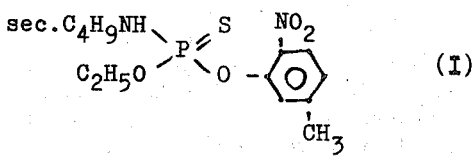
(I)

to the herbicidal composition containing as an active ingredient the compound of the formula (I) and to the use of the compound of the formula,

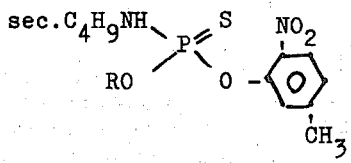

wherein R is methyl or ethyl, as a herbicide.

The present compounds are useful for controlling weeds both in upland and paddy fields, such as grass family weeds, for example barnyard grass, large crab grass, water foxtail, etc. and broad-leaved weeds, for example redroot pigweed, common lambsquater, monochoria, slender spikerush, etc.

The compounds of this invention may be synthetized by reacting a thionophosphoric chloride of the formula,

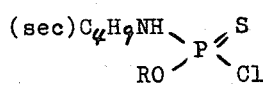

wherein R is as mentioned above with 3-methyl-6-nitrophenol, in an organic solvent in the presence of an acid binding agent.

Examples of the solvents used in this invention include aromatic solvents such as benzene and toluene, and ketones such as acetone and methyl isobutyl ketone, and acetonitrile, etc.

Examples of the acid binding agents include inorganic bases such as potassium carbonate and sodium hydroxide, tertiary amines such as pyridine and triethylamine, and a mixture thereof.

The reaction temperature varies depending on the kind of the solvent or acid binding agent to be used. The reaction is preferably carried out at a temperature of from room temperature to about 120°C. for two to several hours.

Examples of the compounds synthetized by the above method are as follows.

(1) 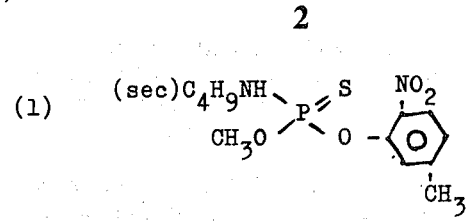

$n_D^{22.0}$ 1.5465

(2) 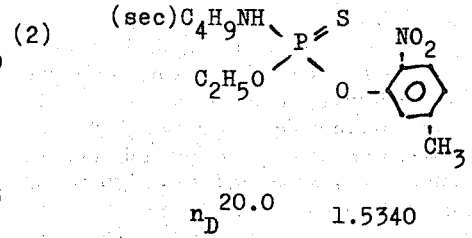

$n_D^{20.0}$ 1.5340

Compounds having similar structure to that of the compounds of this invention are found in U.S. Pat. No. 2,552,576. However, they are different from the compounds of this invention in that they have only nitro group or groups as the substituents for the phenyl group and that their use is directed to insecticides and fungicides.

Also U.S.S.R. Pat. No. 183,743 and Czechoslovak Pat. No. 127,221 describe the present compounds. However, these compounds are described to have only limited use in insecticides, fungicides and miticides and not to have found the excellent herbicidal activity thereof.

Further, Dutch Pat. Nos. 6,916,095 and 6,916,096, U.S. Pat. No. 2,074,790, and Belgian Pat. No. 745,633 describe herbicidal action of compounds having structure resembling that of the compounds of this invention.

Furthermore, U.S. Pat. Nos. 3,472,920 and 3,636,143 also describe herbicidal action of the compounds having structure resembling that of the present compounds. However, they are different in structure from the compounds of this invention.

The present invention have firstly found the excellent herbicidal activity of the compounds of this invention for which 3-methyl, 6-nitro groups on the benzene ring and sec-butyl attached to nitrogen atom are essential.

The herbicidal characteristics of the compounds of the present invention are described in the following:

When subjected to pre-emergence treatment of weeds in paddy field, the compounds display strong herbicidal activities against a wide scope of weeds such as, for example, barnyard grass (*Echinochloa crusgalli*), slender spikerush (*Eleocharis acicularis*), monochoria (*Monochoria viaginalis* Presl.), false pimpernel (*Linderna pyxidaria*), toothcup (*Rotala indica* Koehne), etc. More surprisingly, the compounds can successfully control the aforesaid weeds without any phytotoxicity to transplanted rice seedings. Therefore, the present compounds are quite excellent as herbicides for paddy rice fields. Further, when applied to upland fields, the present compounds have strong herbicidal activities on many weeds, e.g. grass family weeds such as barnyard grass (*Echinochloa crus-galli*), large crabgrass (*Digitaria sanguinalid*), green foxtail (*Setaria viridis*) and water foxtail (*Alopecurus aequalis*), and such broad-leaved weeds as common purslane (*Portulaca oleracea*), redroot pigweed (*Amaranthus retroflexus*), common lambsquarter (*Chenopodium album*) and chickweed (*Stellaria media*), and can effectively control the aforesaid weeds without any phytotoxicity to crops such as, for example, rice, radish, soy bean, pea, carrot and cotton. Therefore, the compounds may be applied to cereals, beans and vegetables, orchards, turfs, pasture lands and non-crop lands.

The present compounds are extremely low in toxicity to mammals and fishes.

In actual application, the compounds of the present invention may be used as they are or may be used in the form of any of such preparations as granules, dusts, wettable powders emulsifiable concentrates, oil spray and aerosol. These preparations are desirably used so as to be in conform to the kinds and sizes of crops and to the purposes of application. In formulating the present compounds, there are used such solid carriers as, for example, talc, bentonite, clay, kaolin, diatomaceous earth, vermiculite and calcium hydroxide; and such liquid carriers as, for example, benzene, alcohols, acetone, xylene, dioxane, methyl naphthalene and cyclohexanone. In actual application, the present compounds may be enhanced and ensured in effectiveness by using them in admixture with surface active agents such as spreaders and stickers and the like. It is also possible to use the present compounds in admixture with fungicides, insecticides, nematocides, other herbicides and the like agricultural chemicals and with fertilizers.

The present invention is illustrated in further detail below with reference to examples. All parts and percentages are by weight.

EXAMPLE 1

25 Parts of the compound (2), 5 parts of a surface active agent of the polyoxyethylene acetylallylester type and 70 parts of talc were thoroughly pulverized and mixed together to obtain a wettable powder.

EXAMPLE 2

30 Parts of the compound (2), 20 parts of an emulsifier of the polyethylene glycol ether type and 50 parts of cyclohexanone were thoroughly mixed together to obtain an emulsifiable concentrate.

EXAMPLE 3

8 Parts of the compound (2), 38 parts of bentonite, 50 parts of clay and 4 parts of sodium lignosulfonate were thoroughly pulverized and mixed together. The resulting mixture was sufficiently kneaded with water, and then granulated and dried to obtain granules.

In order to substantiate the prominent effects of the present compounds as herbicides, detailed illustration is given below with reference to typical test examples, in which the names of the compounds are represented by the numbers of the previously exemplified compounds.

TEST EXAMPLE 1

Pre-emergence application:

Seeds of barnyard grass, large crabgrass, radish, common purslane, redroot pigweed and false pimpernel were individually sowed in flower pots. After covering the seeds with soil, test compounds in such amounts as shown in Table 1 were individually applied to the soil. Thereafter, the test plants were growth in a greenhouse and after 20 days from the application, the herbicidal effects of the individual compounds were investigated to obtain the results as set forth in Table 1. Herbicidal effects were evaluated by the numerals ranging from 0 (not damaged) to 5 (completely killed). All the compounds were formulated into emulsifiable concentrates, and aqueous dilutions thereof were used.

Table 1

| Name of compound | Amount of active ingredient (g./are) | Barnyard grass | Large crabgrass | Radish | Common purslane | Redroot pigweed | False pimpernel |
|---|---|---|---|---|---|---|---|
| (1) | 50 | 5 | 5 | 0 | 5 | 5 | 5 |
|  | 25 | 5 | 5 | 0 | 5 | 5 | 5 |
|  | 12.5 | 4 | 5 | 0 | 5 | 4 | 4 |
|  | 6 | 4 | 4 | 0 | 4 | 4 | 3 |
| (2) | 50 | 5 | 5 | 0 | 5 | 5 | 5 |
|  | 25 | 5 | 5 | 0 | 5 | 5 | 5 |
|  | 12.5 | 5 | 5 | 0 | 5 | 5 | 5 |
|  | 6 | 5 | 5 | 0 | 4 | 4 | 5 |
| 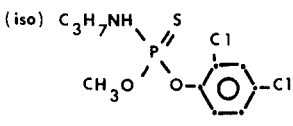 U.S. Pat. No. 3,074,790 | 50 | 5 | 4 | 1 | 2 | 2 | 2 |
|  | 25 | 3 | 2 | 0 | 0 | 1 | 0 |
|  | 12.5 | 1 | 0 | 0 | 0 | 0 | 0 |
|  | 6 | 0 | 0 | 0 | 0 | 0 | 0 |
| 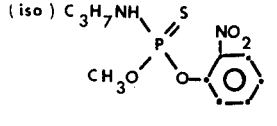 Belgian Pat. 690,911 U.S. Pat. No. 3,472,920 | 50 | 5 | 5 | 2 | 5 | 4 | 4 |
|  | 25 | 3 | 4 | 0 | 4 | 3 | 3 |
|  | 12.5 | 2 | 2 | 0 | 2 | 0 | 1 |
|  | 6 | 0 | 1 | 0 | 0 | 0 | 0 |

Table 1-continued

| Name of compound | Amount of active ingredient (g./are) | Barnyard grass | Large crabgrass | Radish | Common purslane | Redroot pigweed | False pimpernel |
|---|---|---|---|---|---|---|---|
| 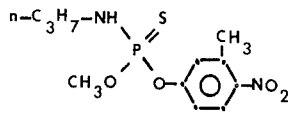 U.S.R. Pat. 183,743 | 50 | 1 | 2 | 0 | 1 | 1 | 1 |
|  | 25 | 0 | 0 | 0 | 0 | 0 | 0 |
|  | 12.5 | 0 | 0 | 0 | 0 | 0 | 0 |
| 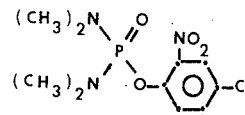 Czech. Pat. 127,221 | 50 | 0 | 0 | 0 | 0 | 0 | 0 |
|  | 25 | 0 | 0 | 0 | 0 | 0 | 0 |
|  | 12.5 | 0 | 0 | 0 | 0 | 0 | 0 |

Herbicidal effects by pre-emergence application.
Herbicidal effects on

TEST EXAMPLE 2

Wagner pots of 14 cm. in diameter, which had been packed individually with 1.5 kg. of paddy field soil, were brought into the state of paddy fields. To the pots were transplanted rice seedings at the 3-leaves stage. Further, seeds of barnyard grass were sowed in the pots and, after covering with soil, the test plants were grown in a greenhouse. On the second day after the sowing given amounts of test compounds were individually applied to the soil under water lodged condition. Broadleaved weeds germinated were monochoria, false pimpernel and toothcup. After 25 days the herbicidal effects and the phytotoxicity thereof to the rice seedings were investigated to obtain the results as set forth in Table 2. The herbicidal effects and the phytotoxicity were evaluated by numerals ranging from 0 (not damaged) to 5 (completely killed).

TEST EXAMPLE 3

Pre-emergence application:

Seeds of redroot pigweed, common purslane, common lambsquarter, starwort sp., mouseear chickweed, annual fleabane, chick weed, bitter cress sp. were individually sowed in flower pots. After covering the seeds with soil, test compounds in such amounts as shown in Table 3 were individually applied to the soil. Thereafter, the test plants were grown in a greenhouse and after 20 days from the application, the herbicidal effects of the individual compounds were investigated to obtain the results as set forth in Table 3. Herbicidal effects were evaluated by the numerals ranging from 0 (not damaged) to 5 (completely killed). All the compounds were formulated into emulsifiable concentrates, and aqueous dilutions thereof were used.

The results are as follows.

Table 2

Herbicidal effects in application under waterlodged conditions.

| Name of compound | Amount of active ingredient (g./are) | Barnyard grass | Broadleaved weeds | Phytotoxicity on rice |
|---|---|---|---|---|
| (1) | 50 | 5 | 5 | 0 |
|  | 25 | 5 | 5 | 0 |
|  | 12.5 | 4 | 5 | 0 |
| (2) | 50 | 5 | 5 | 0 |
|  | 25 | 5 | 5 | 0 |
|  | 12.5 | 5 | 5 | 0 |
| 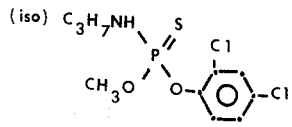 U.S. Pat. No. 3,074,790 | 50 | 4 | 2 | 1 |
|  | 25 | 2 | 0 | 0 |
|  | 12.5 | 0 | 0 | 0 |

Table 3

| Name of compound | Amount of active ingredient (g./are) | Redroot pigweed | Common purslane | Common lambsquarter | Starwort sp. | Mouseear chickweed | Annual fleabane | Chick weed | Bitter cress sp. | Bed straw | Pale smart weed | Carpet weed sp. | Speedwell sp. |
|---|---|---|---|---|---|---|---|---|---|---|---|---|---|
| (1) | 10 | 5 | 5 | 4 | 5 | 5 | 5 | 5 | 4 | 4 | 4 | 5 | 4 |
|  | 5 | 4 | 4 | 4 | 4 | 4 | 4 | 4 | 4 | 4 | 3 | 3 | 4 |

Table 3-continued

| Name of com- pound | Amount of active ingredient (g./are) | Red- root pig- weed | Common purs- lane | Common lambs- quarter | Star- wort sp. | Mouse- ear chick- weed | Annual flea- bane | Chick weed | Bitter cress sp. | Bed straw | Pale smart weed | Carpet weed sp. | Speed- well sp. |
|---|---|---|---|---|---|---|---|---|---|---|---|---|---|
| (2) | 10 | 5 | 5 | 5 | 5 | 5 | 5 | 5 | 5 | 5 | 5 | 5 | 5 |
|     | 5  | 4 | 4 | 5 | 4 | 5 | 4 | 5 | 4 | 4 | 4 | 4 | 4 |
| (A) | 10 | 2 | 1 | 2 | 1 | 1 | 0 | 1 | 1 | 1 | 1 | 1 | 1 |
|     | 5  | 1 | 0 | 1 | 0 | 0 | 0 | 1 | 0 | 0 | 0 | 0 | 0 |

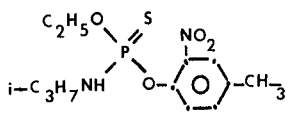

(A) =   The strongest compound in U.S. Patent No. 3,636,143.

Certain organophosphorous compounds tend to destroy or remove myelen from nervus system and have delayed neurotoxicity toward human being thereby causing polyneuritis and especially paralysis at legs. TOCP (tri ortho cresyl phosphate) is a typical example of such compounds, which is said to cause Jamaica ginger paralysis. This impediment can be experimentally reproduced with a highest sensitivity in hens.

The present inventors have examined the toxicities of the present compounds and the closely related reference compounds. The results are as follows.

TEST EXAMPLE 4

Hens (age 1–1.5 years) were used as test animals. For each test compound, a suspension was made with a 10% Tween 80 solution, and orally administered to hens in an amount of 1.0 ml./kg. body. Five weeks after the administration the toxic symptoms and death were observed. The leg paralysis was determined by the ataxia. When the acute toxic symptoms are extreme the observation was made while treating by administering 10 mg./kg. of atropine sulfate and 50 mg./kg. of PAM (pyridine-2-aldoxime methiodide). The results are shown in Table 1.

Table 4

| Compound | Administered dosage (mg./kg.) | Number of tested hens | Dead in 48 hrs. | Number of hens with leg paralysis after 2 weeks | Occurrence of leg paralysis (%) |
|---|---|---|---|---|---|
| (sec)BuNH–P(=S)(OEt)–O–C6H3(NO2)(CH3) | 250 | 1 | 0 | 0 | 0 |
|  | 500 | 1 | 0 | 0 | 0 |
|  | *750 | 7 | 0 | 0 | 0 |
| (sec)BuNH–P(=S)(OMe)–O–C6H3(NO2)(CH3) | 250 | 5 | 0 | 0 | 0 |
|  | *500 | 7 | 1 | 0 | 0 |
| (iso)PrNH–P(=S)(OC2H5)–O–C6H3(NO2)(CH3)  U.S.P. 3,636,143 | 250 | 7 | 0 | 4 | 57 |
|  | 500 | 7 | 0 | 7 | 100 |
| (iso)PrNH–P(=S)(OCH3)–O–C6H3Cl2  U.S.P. 3,074,790 | 500 | 1 | 0 | 0 | 0 |
|  | 1000 | 5 | 1 | 4 | 100 |

*treated by administering atropine sulfate and PAM

As shown in Tables 1, 2 and 3, the herbicidal activities of the present compounds are superior to those of reference compounds. Especially, to broadleaved weeds the present compounds have higher activity than the reference compound (A) described in U.S. Pat. No. 3,636,143 which closely relates to the present compounds.

Further as shown in Table 4, the reference compounds showed neurotoxicity towards hens, but on the contrary the present compound did not show any neurotoxicity at all.

It seems that those good characteristics are due to particular substituents of 3-methyl, 6-nitro on the benzene ring and N-secondary butyl.

What we claim is:
1. A phosphorothionoamidate of the formula:

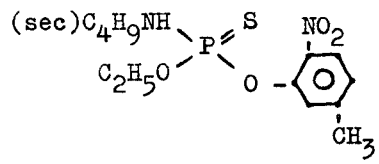

* * * * *